United States Patent [19]

Donovan

[11] Patent Number: 4,792,611

[45] Date of Patent: Dec. 20, 1988

[54] CYCLIC N-HYDROXYIMIDE DETERGENT ADDITIVES

[75] Inventor: Stephen F. Donovan, Fairfield, Conn.

[73] Assignee: American Cyanamid Company, Stamford, Conn.

[21] Appl. No.: 84,241

[22] Filed: Aug. 12, 1984

[51] Int. Cl.[4] .......................................... C07D 207/46
[52] U.S. Cl. .................................. 548/542; 252/117; 252/542
[58] Field of Search .......................................... 548/542

[56] References Cited

PUBLICATIONS

Katritzky et al., "Chemistry of the Heterocyclic N-Oxides", Academic Press, N.Y., N.Y., (1971), p. 105.

Primary Examiner—Glennon H. Hollrah
Assistant Examiner—D. B. Springer
Attorney, Agent, or Firm—Michael J. Kelly; Steven H. Flynn

[57] ABSTRACT

Cyclic N-hydroxyimide compounds derived from tartaric acid are provided which exhibit strong metal ion chelating ability, making them useful as detergent additives, in boiler water systems, as reaction intermediates, etc. A detergent composition containing N-hydroxyimide compounds as detergent additives is also disclosed.

7 Claims, No Drawings

CYCLIC N-HYDROXYIMIDE DETERGENT ADDITIVES

The present invention relates to chelating agents useful, e.g., as adjuvants for detergent compositions, particularly fabric-washing detergent compositions. In particular it relates to novel cyclic N-hydroxyimides useful as detergent additives and to detergent compositions comprising at least one detersive surfactant and an effective amount of an N-hydroxyimide detergent additive.

BACKGROUND OF THE INVENTION

Detergent compositions have long employed materials, known as "builders", to improve the detergency of soaps and synthetic detergents by actively chelating alkali metal cations which are normal components of "hard" tap water. Such builders have been found to affect, for instance, soil suspension, emulsification of soil particles, solubilization of water-insolubles, and inactivation of various mineral constitutents present in a detergent system. Many materials useful as builders have been proposed, and their effects are known. See, e.g., U.S. Pat. Nos. 3,852,213, 3,950,260, 4,182,718, and 4,440,646 (all incopporated herein by reference).

Recently, however, the attention of detergent manufacturers and researchrrs has turned to the role of heavier metal cations, i.e., transition metal cations and particularly iron, in the formation of stain complexes on fabrics and other surfaces. It has been observed that these multivalent transition metal cations, particularly iron ($Fe^{+++}$), enhance the binding of the components of many stains to substrates, and breaking up the cation-enhanced bonds is an effective approach to stain removal. Therefore, there is a strong need for the discovery of new materials that are effective as chelating agents for transition metal cations, are easy to prepare, and can be added to detergent compositions in economical amounts to boost stain-removing power.

It has now been discovered that certain cyclic N-hydroxyimides add their salts derived from tartaric acid esters are active chelants of metal ions, particularly $Fe^{+++}$, and are useful as detergent additives because of their stain-removing ability. As an additional advantage, the N-hydroxyimides of the present invention are believed to be broken down in freshwater systems to tartaric acid, which is well known to be biodegradable.

SUMMARY OF THE INVENTION

It is therefore an object of the present invention to provide a new class compounds which are useful as transition metal ion chelating agents.

It is a further object of the present invention to provide detergent additives effective in stain removal.

It is a further object of the present invention to provide a detergent additive that is biodegradable.

It is a further object of the present invention to provide a novel detergent composition.

It is a further object of the present invention to provide a fabric-washing detergent composition that is effective in stain removal.

These and other objects are achieved, according to the present invention, by cyclic N-hydroxyimide compounds having the formula

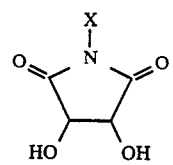

where X is —OH or —O$^-$M$^+$, where M$^+$ is an alkali metal or ammonium cation.

Also contemplated herein are detergent compositions comprising one or more detersive surfactants and one or more detergent additives consisting essentially of cyclic N-hydroxyimide compounds having the formula

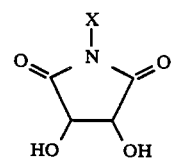

where X has the same meaning as above.

DETAILED DESCRIPTION OF THE INVENTION

The N-hydroxyimide compounds of the present invention are advantageously prepared from tartaric acid, e.g., by first reacting it with an alkanol to form a tartrate ester, then reacting the tartrate ester with hydroxylamine or a salt thereof to obtain the N-hydroxyimide compounds of the present invention. A typical reaction scheme for the preparation of detergent compounds according to the present invention is as follows:

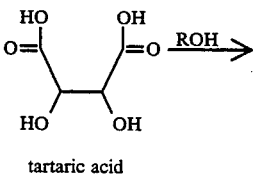

tartaric acid

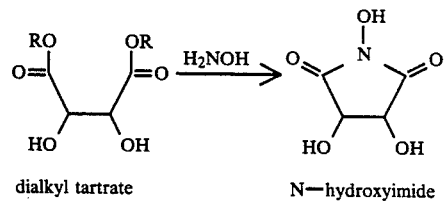

dialkyl tartrate    N—hydroxyimide

Tartaric acid, especially L-tartaric acid or "natural" tartaric acid (L-2,3-dihydroxybutanedioic acid), is widely distributed in nature and occurs in many fruits. In modern processes it is obtained as a byproduct of the wine-making industry from potassium tartrate, a crystalline deposit from fermentation, which is converted to the calcium salt, then hydrolyzed to tartaric acid and calcium sulfate.

In order to prepare the dialkyl tartrate esters which are the preferred starting materials in preparing the N-hydroxyimide compounds of the present invention, dehydrated tartaric acid is reacted with an alkanol of from 1 to 6 carbons, e.g., methanol, ethanol, propanol, isopropanol, butanol, isobutanol, etc. The amount of alkanol employed will normally be a large stoichiometric excess in order to ensure esterification of both carboxyl groups of the dicarboxylic acid substrate. Most advantageously, the tartaric acid is simply dissolved in a suitable quantity of the alkanol, e.g., 2-20 moles alkanol per mole of tartaric acid.

Reaction of the dialkyl tartrate ester to obtain N-hydroxyimide products may be accomplished by contacting the ester with at least a substantially equimolar quantity of hydroxylamine. A hydroxylamine salt, preferably hydroxylamine hydrochloride, can be used, and it will be necessary to neutralize the salt (which is unreactive toward the esters) and generate free hydroxylamine for the reaction to proceed. The reaction will therefore normally be carried out in the presence of about 1-5 moles per mole of hydroxylamine of a basic agent, preferably an organic base such as sodium ethoxide, pyridine, triethylamine, or quinoline. Most preferably, the reaction will be carried out in an alcoholic solvent, such as ethanol. The raaction takes place at room temperature and is completed in several hours, e.g., 2-20 hours.

The product may be isolated in any one of a number of known ways. For example, the product can be isolated by precipitation from a non-solvent, such as hexane, and the precipitate filtered, washed and dried under vacuum to give the cyclic N-hydroxyimide product.

Alternatively, flash or spray drying may be used. The drying step removes substantially all of the organic base, and washing with alcoholic hydrogen chloride effectively scavenges residual amounts, in cases where complete removal of the basic agent is required.

The cyclic N-hydroxyimide compounds are active chelating agents with respect to transition metal cations, especially iron, and are advantageously included in a detergent composition, in accordance with the present invention. A detergent composition of this invention will contain at least one detersive surfactant. Such surfactants will be present in amounts usually encountered in detergent compositions, e.g., from about 1 to about 50% by weight, preferably about 5 to about 25% by weight for fabric-washing detergents, and most preferably from about 10 to about 20% by weight based on the total weight of the detergent composition. The surfactants may be anionic, nonionic, cationic or amphoteric, and mixtures of different detersive surfactants may be used. Non-limiting examples of suitable detersive surfactants include:

(a) Anionic surfactants: soaps, i.e., alkali metal (preferably sodium or potassium) salts of long-chain fatty acids containing from 8 to 20 carbon atoms, such as lauric, myristic, oleic, palmitic, capric, caprylic, and stearic acids, used singly or in mixtures of differing chain lengths; alkali metal salts of organic sulfuric reaction products having long hydrocarbon chains of about 8 to about 20 carbon atoms and a radical selected from the group consisting of sulphonic acid and sulfuric acid ester radicals, such as sodium or potassium alkyl sulphates, preferably those obtained by sulphating higher ($C_8$-$C_{18}$) alcohols; sodium or potassium alkyl benzenesulphonates in which the alkyl group contains from about 9 to about 20 carbon atoms, such as sodium linear alkyl ($C_{10}$-$C_{15}$) secondary benzenesulphonate, 2-phenyl-dodecanesulphonate, 2-phenyl-octadecanesulphonate and 3-phenyl-dodecanesulphonate; alkali metal (preferably sodium) olefin sulphonates, i.e., the mixture of detersive surfactants obtained from sulphonation of $C_8$-$C_{22}$ olefins, preferably straight-chain alpha-olefins; sodium alkyl glyceryl ether sulphonates, including ethers of higher alcohols derived from tallow coconut oil and synthetic alcohols derived from petroleum; sodium coconut oil fatty acid monoglyceride sulphates and sulphonates; sodium or potassium salts of sulfur acid esters of the reaction between higher fatty alcohols (e.g., tallow or coconut oil alcohols) and ethylene oxide; the esterification products of fatty acids with isethionic acid, neutralized with sodium hydroxide; and sodium or potassium salts of fatty acid amides of methyl taurine.

(b) Nonionic synthetic detersive surfactants: compounds formed by condensing ethylene oxide with a hydrophobic base formed by the condensation of propylene oxide with propylene glycol; the polyethylene oxide condensates of alkyl-phenols, e.g., the condensation products of alkyl-phenols, having an alkyl group containing from about 6 to 12 carbon atoms in either a straight or branched chain, with ethylene oxide, said ethylene oxide being present in amounts equal to 5 to 25 moles of ethylene oxide per mole of alkylphenols (the alkyl substituent in such compounds may be derived from polymerised propylene, diisobutylene, octene, dodecene, or nonene, for example); compounds derived from the condensation of ethylene oxide with the product resulting from the reaction of propylene oxide and ethylenediamine, such as compounds containing from about 40% to about 80% polyoxyethylene by weight and having a molecular weight of from about 5,000 to about 11,000 resulting from the reaction of ethylene oxide groups with a hydrophobic base constituted of the reaction product of ethylenediamine and excess propylene oxide, said hydrophobic base having a molecular weight of the order of 2,500 to 3,000; the condensation product of aliphatic alcohols having from 8 to 18 carbon atoms, in either straight chain or branched chain configuration, with ethylene oxide, e.g., a coconut alcohol-ethylene oxide condensate having from 6 to 30 moles of ethylene oxide per mole of coconut alcohol, the coconut alcohol fraction having from 10 to 14 carbonaatoms; long chain tertiary amine oxides corresponding to the following general formula, $R^1R^2R^3N=O$, wherein $R^1$ is an alkyl radical of from about 8 to 18 carbon atoms and $R^2$ and $R^3$ are each methyl, ethyl or hydroxyethyl radicals, such as dimethyldodecylamine oxide, dimethyloctylamine oxide, dimethyldecylamine oxide, diethyltetradecylamine oxide and dimethylhexadecylamine oxide, N-bis (hydroxyethyl)dodecylamine oxide; long chain tertiary phosphine oxides corresponding to the following formula $R^4R^5R^6P=O$, wherein $R^4$ is an alkyl, alkenyl or monohydroxyalkyl radical of 10 to 18 carbon atoms and $R^5$ and $R^6$ are each alkyl or monohydroxyalkyl groups containing from 1 to 3 carbon atoms, such as dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, bis(hydroxymethyl)dodecylphosphine oxide, bis(2-hydroxyethyl)dodecylphosphine oxide, 2-hydroxypropylmethyltetradecylphosphine oxide, dimethyloleylphosphine oxide, and dimethyl-2-hydroxydodecylphosphine oxide; and dialkyl sulphoxides corresponding to the following formula, $R^{78}S=O$, wherein $R^7$ is an alkyl, alkenyl, beta- or gamma-monohydroxyalkyl radical or an alkyl or beta- or gamma-monohydroxyoxyalkyl radical containing one or two other oxygen atoms in the chain, the $R^7$ groups ranging from 10 to 18 carbon atoms in chain length, and wherein $R^8$ is methyl, ethyl or alkylol, such as dodecyl methyl sulphoxide, tetradecyl methyl sulphoxide, 3-hydroxytridecyl methyl sulphoxide, 2-hydroxydodecyl methyl sulphoxide, 3-hydroxy-4-decyloxybutyl methyl sulphoxide, 3-hydroxy-4dodecyloxybutyl methyl sulphoxide, 2-hydroxy-3decyloxypropyl methyl sulphoxide, 2-hydroxy-3-dodecyloxypropyl methyl sulphoxide, dodecyl ethyl sulphoxide, 2-hydroxydodecyl ethyl sulphoxide, dodecyl-2-hydroxy ethyl sulphoxide.

(c) Ampholytic synthetic surfactants: derivatives of aliphatic secondary and tertiary amines, in which the aliphatic radical may be straight chain or branched chain and wherein one of the aliphatic substituents contains from about 8 to 18 carbon atoms and one contains an anionic water solubilizing group, such as sodium-3-dodecylaminopropionate, sodium-3-dodecylaminopropanesulphonate and sodium N-2-hydroxydodecyl-N-methyl-taurate.

(d) Zwitterionic synthetic surfactants: derivatives of aliphatic quaternary ammonium compounds, sulphonium compounds and phosphonium compounds in which the aliphatic radical may be straight or branched chain and wherein one of the aliphatic substituents contains from about 8 to 18 carbon atoms and one contains an anionic water solubilizing group, such as 3-(N,N-dimethyl-N-hexadecylammonio)propane-1-sulphonate, 3-(N,N-dimethyl-N-hexadecylammonio)-2-hydroxypropane-1-sulphonate, 3-(dodecylmethylsulphonium) propane sulphonate, and 3-(cetylmethylphosphonium) ethane sulphonate.

The detergent compositions of the present invention will contain, besides one or more detersive surfactants, about 3% to about 12% by weight of the composition, preferably about 6% by weight, of the cyclic N-hydroxyimide compounds described above.

In addition to the surfactants and the cyclic N-hydroxyimide chelants, the detergent composition may also contain coventional detergent builders such as condeneed phosphates, trisodium nitrilotriacetate (NTA), sodium carbonate, zeolites, sodium silicates, etc., and organic polymers such as polyacrylates, polymaleates and polymethacrylates. See, e.g., U.S. Pat. Nos. 3,393,150, 36666,664, 3,707,502, 3,839,215 and 4,067,816, which are incorporated herein by reference. The combined detergent builders will make up from about 10% to about 50% by weight of the detergent composition. In addition to the essential detersive surfactants and detergent additives, a detergent composition of the invention may comprise such conventional ingredients as lather boosters (e.g., alkanolamides), fillers, antiredeposition agents, fluorescers, pigments, germicides, scents, and enzymes.

A detergent composition according to the invention can be prepared by any conventional manufacturing technique used for preparing detergent compositions, such as slurry making and spray-drying, and the detergent can take anyone of the common physical forms associated with detergents, such as powders, flakes, granules, noodles, cakes, bars and liquids.

Liquid detergent compositions according to the invention will most preferably be a concentrated aqueous solution having a basic pH, at least about pH 8, most preferably pH 9 or above, comprising one or more of the detersive surfactants described above and one or more cyclic N-hydroxyimide compounds of this invention.

The invention is further illustrated by the following examples, which should not be contrued as limiting the scope of the invention.

EXAMPLE 1

An alcoholic hydroxylamine/sodium ethoxide reactant solution was prepared as follows: 15 g (0.65 moles) of metallic sodium were added to 300 ml of absolute ethanol under nitrogen gas. A separate hydroxylamine solution was prepared by adding 22.5g (0.326 moles) of hydroxylamine hydrochloride to 500 ml of absolute ethanol. The two solutions were mixed at 40° C., then cooled to 5° and filtered.

26.7 g (0.15 moles) of the L-dimethyl tartrate were added to the hydroxylamine/sodium ethoxide solution. The reaction mixture was allowed to stand at room temperature overnight.

The ethanol was removed by rotary evaporator at reduced pressure, then 500 ml water and 200 ml of hexane were added to the reaction mixture, which was shaken and allowed to separate into two layers. The aqueous layer was freeze dried to give 36.59 g of a light yellow powder.

Infrared and nuclear magnetic resonance spectra and high pressure liquid chromatography (pH 7.0 with UV detector set at 270 nm) indicated that the product had the following structure:

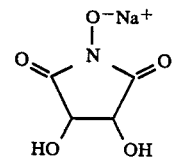

sodium salt of N—hydroxy-(3R—trans)-
3,4-dihydroxy-2,5-pyrrolidinedione

EXAMPLE 2

The procedure of Example 1 was carried out in the same manner, except that 10.0 g of sodium (0.43 moles) were used in preparing the sodium ethoxide solution, and 15.0 g of hydroxylamine hydrochloride (0.22 moles) were used. The yield was 34.46 g of the sodium salt of N-hydroxy-(3R-trans)-3,4-dihydroxy-2,5-pyrrolidinedione.

EXAMPLE 3

The performance of the N-hydroxyimide compounds of Examples 1 and 2 as fabric-washing detergent additives was examined in a tea stain removal test:

Swatches of white cotton cloth were boiled in very strong tea (10 tea bags/1 liter dionized water), brewed 10 min.) for 15 minutss. The tea solution and swatches were removed from the heat and cooled to 115° F. with continued stirring. The swatches were thereafter wrung and air dried between paper towels.

Deionized water was heated to 40° C. and 0.1 g of $CaCl_2$ were added per each liter of water, followed by 1.5 g per liter of water of a commercial fabric-washing detergent (Tide ®; Procter & Gamble).

To 1-liter aliquots of this detergent solution were added 100 mg of the detergent additives to be tested, which were stirred until dissolved. The wash solutions were maintained at about 35° C. add a stirring speed of 100 rpm. The pH was adjusted to 10 if necessary with sulfuric acid or sodium hydroxide. Tea stained swatches of cloth were added to each test solution and stirred rapidly for 10 minutes, after which the solution was poured off and the swatches squeezed out and rinsed for 2 minutes in deionized water containing the same proportion of CaCl$_2$. The swatches were then air dried overnight and compared against a control and a commercial detergent additive.

The detergent additives of Examples 1 and 2 were compared against a control (no additive) and a commercial detergent additive (Dequest ® 2041; Monsanto). After the complete wash cycle, the swatches of the control solution appeared darkest, and the comparison sample and the samples using the detergent builders of Examples 1 and 2 appeared visibly lighter.

It will be understood that the foregoing description of the invention is susceptible to modifications, changes and adaptations, all of which are intended to be comprehended within the meaning and range of equivalents of the appended claims. For instance, though the foregoing description is directed to the use of the N-hydroxyimides in detergent systems, they will also find application in boiler water systems and other scale prevention uses, polymerization intermediates, and other embodiments where strong transition metal ion chelation is required.

I claim:

1. A cyclic N-hydroxyide compound having the formula

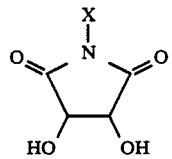

wherein X is —OH or —O$^-$M$^+$, where M$^+$ is an alkali metal or ammonium cation.

2. A compound according to claim 1 consisting essentially of N-hdyroxy-(3R-trans)-3,4-dihydroxy-2,5-pyrrolidinedione or an alkali metal or ammonium salt thereof.

3. A detergent additive prepared by reacting a $C_1$-$C_6$ dialkyl ester of tartaric acid with hydroxylamine or a salt thereof in the presence of an organic base until a cyclic N-hydroxyimide compound as define in claim 1 is obtained.

4. A detergent additive according to claim 3, wherein the dialkyl ester is reacted with hydroxylamine hydrochloride in the presence of an organic base.

5. A detergent additive according to claim 3, wherein the organic base is sodiium ethoxide.

6. A detergent additive according to claim 3, wherein a $C_1$-$C_6$ dialkylester of L-2,3-dihydroxybutanedioic acid is reacted in a solution of hydroxylaminehhydrochloride and 1-5 moles, per mole of hydroxylamine hydrochloride, of sodium ethoxide in ethanol for a period of about 4-20 hours until a sodium salt of N-hydroxy-(3R-trans)-3,4-dihydroxy-2,5-pyrrolidinedione is obtained.

7. A detergent additive prepared by reacting an ester selected from diemthyl, diethyl, dipropyl, diisopropyl, dibutyl or diisobutyl tartrate or L-tartrate with hydroxylamine or hydroxylamine hydrochloride in the presence of an organic base selected from sodium ethoxide, pyridine, triethylamine, or quinoline until a cyclic N-hydroxyimide is obtained.

* * * * *

UNITED STATES PATENT AND TRADEMARK OFFICE
CERTIFICATE OF CORRECTION

PATENT NO. : 4,792,611
DATED : December 20, 1988
INVENTOR(S) : Stephen F. Donovan It is certified that error appears in the above-identified patent and that said Letters Patent is hereby corrected as shown below:

On the title page, Item [22], "Aug. 12, 1984" should read -- Aug. 12, 1987 --.

Signed and Sealed this

Nineteenth Day of December, 1989

Attest:

JEFFREY M. SAMUELS

*Attesting Officer*  *Acting Commissioner of Patents and Trademarks*